United States Patent [19]
Radisson

[11] Patent Number: 5,981,809
[45] Date of Patent: *Nov. 9, 1999

[54] PROCESS FOR THE PREPARATION OF DIFUNCTIONAL COMPOUNDS OF HIGH ENANTIOMERIC PURITY

[75] Inventor: Xavier Radisson, Lyons, France

[73] Assignee: Rhone-Poulenc Chimie, Courbevoie Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/553,675

[22] PCT Filed: Jun. 8, 1994

[86] PCT No.: PCT/FR94/00673

§ 371 Date: Mar. 4, 1996

§ 102(e) Date: Mar. 4, 1996

[87] PCT Pub. No.: WO94/29253

PCT Pub. Date: Dec. 22, 1994

[30] Foreign Application Priority Data

Jun. 11, 1993 [FR] France .................................. 93 07280

[51] Int. Cl.$^6$ ...................... C07C 29/147; C07C 29/143; C07C 29/14; C07C 319/02; C07C 319/12

[52] U.S. Cl. .............................. 568/864; 568/62; 568/66; 568/861; 568/862

[58] Field of Search ............................... 568/62, 66, 861, 568/862, 864

[56] References Cited

U.S. PATENT DOCUMENTS

| | | | |
|---|---|---|---|
| 4,088,666 | 5/1978 | Langer et al. | 568/861 X |
| 4,945,187 | 7/1990 | Muller | 568/864 X |
| 5,196,601 | 3/1993 | Kitsuki et al. | 568/861 X |

FOREIGN PATENT DOCUMENTS 0350852  1/1990  European Pat. Off. .

OTHER PUBLICATIONS

Melchiorre, C. "A Convenient Synthesis of S(+)–propane–1, 2–diol." Chemistry and Industry (Mar. 6, 1976): 218.

Gombos, J. et al. "Notiz über eine einfache Herstellung von (S)–Propylenoxid." Chem. Ber. (1976): 109, 2645–2647.

Primary Examiner—Michael G. Ambrose
Attorney, Agent, or Firm—Burns, Doane, Swecker & Mathis, L.L.P.

[57] ABSTRACT

A process for preparing a difunctional compound having high enantiomeric purity that is a 1,2-, 1,3-, or 1,4-diol, dithiol, or mercapto alcohol from an optically active starting material that includes an $\alpha$-, $\beta$-, or $\gamma$-hydroxy (or mercapto) aldehyde, ketone, ester, or amide is described. The process is carried out in an anhydrous solvent medium and comprises (1) reducing the starting material with a metal hydride (e.g., sodium borohydride), (2) adding a coreactant that is substituted by at least one, but preferably two, hydroxyl or mercapto groups (e.g., pyrocatechol), and (3) directly distilling the product from the reaction medium. The coreactant preferably has a higher boiling point at normal atmospheric pressure than the difunctional compound. The difunctional compounds are used as reactants for syntheses of agrochemicals or pharmaceuticals, or as precursors for polymers.

34 Claims, No Drawings

PROCESS FOR THE PREPARATION OF DIFUNCTIONAL COMPOUNDS OF HIGH ENANTIOMERIC PURITY

The field of the invention is that of enantiomers, in particular difunctional ones, of high optical purity.

This purity is particularly interesting and advantageous in view of the optimum expression of the functionalities of the enantiomers, especially as reactants, synthons or intermediates in specific syntheses of chiral compounds such as active ingredients, e.g. pharmaceutical or agrochemical ones, or as active compounds per se or else as precursors of special polymers.

More precisely, the present invention relates to the synthesis of difunctional compounds of high enantiomeric purity and of formula:

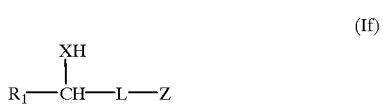
(If)

in which:

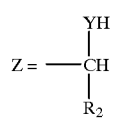

$R_1$ and $R_2$ are identical or different and denote hydrogen or an aliphatic and/or alicyclic and/or aromatic and/or heterocyclic hydrocarbon radical, preferably a hydrogen or an alkyl, X and Y are identical or different and denote oxygen or sulphur, and L denotes a σ covalent single bond or a $C_1$ or $C_2$ alkyl group, from pure chiral compounds corresponding to the formula (Id), which corresponds to the formula (If) in which:

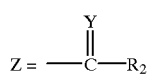

with $R_2$ and Y as defined above, it being additionally possible for $R_2$ to denote an $NH_2$, alkoxy, or alkylated S radical or:

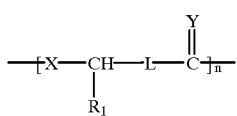

with n=1 to 1000.

Still more precisely the present invention relates to the synthesis of enantiomers of high optical purity containing at least two hydroxyl functional groups (diols) or two thiol functional groups (dithiols).

A nonlimiting example of a diol is (+)(S)-1,2-propanediol or (−)(R)-1,2-propanediol.

To obtain enantiomers of high optical purity the operation is conventionally carried out by resolving the racemate: a chemical or enzyme route. The chemical route is essentially that of converting the racemate to two separable diastereoisomers. Separation by liquid phase chromatography or by crystallization may be mentioned.

These chemical resolutions are cumbersome, complex and therefore costly to implement.

The same applies to enzyme resolutions which, in addition, present the disadvantage of being specific to a given enantiomer.

Routes for specific asymmetric chemical synthesis are also known, like, for example, the asymmetric dihydroxylation of propene, catalysed by osmium tetraoxide and making it possible to obtain one of the enantiomers of 1,2-propanediol (K. B. Sharpless et al., J.O.C., 1992, 57, 2768), with an enantiomeric purity which remains moderate.

Another, more advantageous, possibility of obtaining compounds of high enantiomeric purity, which are capable of being exploited industrially, consists in employing chiral compounds as starting materials, like, for example, those corresponding to the formula (Id) given above, and in reducing them so as to produce the hydrogenated derivatives of high enantiomeric purity which are aimed at (If).

By definition, the chiral materials (Id) are inexpensive, being easily available or accessible. They may be materials which are present in nature and are easily extractable, or else compounds that can be produced in industrial quantities, e.g. by fermentation or resolution. These materials (Id) are, for example, esters of α-, β- or γ-hydroxycarboxylic acids or of other derivatives of the latter, such as ketones or aldehydes, as well as their equivalents, when sulphur is substituted for oxygen in the radicals X and Y.

Among these techniques employing a reduction, those using catalytic reduction under hydrogen will be adopted, as well as those using stoichiometric reduction with the aid of a chemical reducing agent.

Insofar as the catalytic reduction under hydrogen is concerned, the prior technical literature bears witness to the great difficulties that exist in reducing an acid, an ester, an aldehyde, a ketone, or their sulphur analogues, to alcohol or thiol in conditions that are mild and productive. The catalysts employed in heterogeneous catalysis are generally Raney nickel and copper chromites.

By way of example, the paper by E. Bowden et al., JACS, 56, 689, 1934, may be cited, which is one of the only ones to be concerned with chirality and which reports a total racemization when (+)n-butyl lactate is subjected to reduction by heterogeneous catalysis with the aid of copper chromite (200 bars-225° C.-2 hours in bulk).

It must therefore be concluded that the reaction conditions imposed by catalytic reduction are too drastic and, consequently, entail a racemization or a loss of chirality of the final products obtained by reduction of hydroxycarboxylic acids, their esters, hydroxyketones or hydroxyaldehydes.

Moreover, it is appropriate also to report the low output efficiency of these catalytic reduction techniques.

Stoichiometric reduction using a chemical reducing agent consists, essentially, of the use of hydrides as reducing agents.

The hydrides chiefly concerned are lithium borohydride ($LiBH_4$), sodium borohydride ($NaBH_4$), potassium borohydride ($KBH_4$), lithium aluminium hydride ($LiAlH_4$) or diisobutyl aluminium hydride (DiBAH).

There are many scientific publications which deal with the reduction, with the aid of hydrides, of pure enantiomers of alpha-hydroxycarboxylic acids or of their esters (lactic acid/lactate) to more or less pure enantiomers of the diol type: 1,2-propanediol.

The paper by Barnett and Kent, JCS, 2743-510 (1963), may be mentioned by way of example, describing the conversion of methyl pyruvate in an alcoholic medium at 20° C. and in the presence of potassium borohydride, into a mixture of methyl lactate and 1,2-propanediol. In this reaction the metal complexed with the hydrogen in the hydride (boron) binds to the substrate, and therefore to the final product. This makes it necessary to displace the metal complex thus formed (borate) by a treatment consisting, first of all, in diluting with methanol and acidifying with an acidic methanolic solution of HCl. Methyl borate is thus formed, which is distilled off at atmospheric pressure. It is then necessary to neutralize the solution with the aid of lead carbonate and to filter and to concentrate at reduced pressure the product, which is finally extracted by fractional distillation or by entrainment with chloroform. According to another alternative form the final product is extracted by entrainment with an ether-water solvent system and fractional distillation.

Such a technique does not make it possible to attain good yields and, furthermore, requires long purification and extraction treatments which are cumbersome and complex to carry out.

Melchiorre, in Chemistry and Industry, Mar. 6, 1976, page 218, describes a synthesis of S(+)-1,2-propanediol from S(+)-lactic acid and in the presence of diborane. The solvent medium employed is tetrahydrofuran. The removal of the excess diborane is performed by adding water and displacing the boron/propanediol complex by rinsing with anhydrous methanol, this solvent giving rise to a transesterification and formation of trimethyl borate. The solvent is next evaporated off. This dilution-evaporation operation is repeated until the boron is completely eliminated.

Besides the fact that diborane is a reactant which is hazardous to handle, the fact of involving water necessarily limits the yields, because esters of boron and of 1,2-propanediol are extremely soluble in this solvent, resulting in undoubted difficulties in extraction. Melchiorre's yield is, in fact, only 75%, while the optical purity of the enantiomer obtained is $[\alpha]_D^{25}=+15.84°$, that is, an enantiomeric excess:

$$ee = \frac{\text{proportion of major enantiomer} - \text{proportion of minor enantiomer}}{\text{proportion of major enantiomer} + \text{proportion of minor enantiomer}} = 92,$$

which remains relatively low.

Finally, it should be pointed out that the methanolic dissolving/evaporation procedure is not really industrial.

As a final illustration of the state of the art it is appropriate to mention U.S. Pat. No. 4,945,187, which describes a process for the preparation of pure enantiomers of S(+)-1,2-propanediol and of R(−)-1,2-propanediol from L(−)-lactide and D(+)-lactide respectively. Here the reduction is performed in toluene with the aid of diisobutylaluminium hydride (DiBAH). The displacement of the complex with the hydride residues is performed by hydrolysis with the aid of NaOH, and then by precipitation with aluminium hydroxide in aqueous solution at acidic pH. The enantiomers are then recovered by evaporation, washing with ethanol and then distillation.

Water, with all its penalizing implications, is still employed in this process which, furthermore, comprises many stages which are long and complex to implement and which are therefore, finally, difficult to implement industrially.

From the above it clearly follows that there is a lack of a process for the preparation of enantiomers of high optical purity, that is to say which have an enantiomeric excess ee higher than 95%, of compounds of the diol or dithiol or else mono-OH and mono-SH type from derivatives of α-, β- or γ-, preferably α-hydroxycarboxylic acids, such as esters, cyclic dimers, ketones or aldehydes, which is:

economical, easy to implement, rapid, and which meets the industrial constraints of high yield and high output efficiency.

One of the objectives of the present invention is therefore to remedy this lack by providing a process for the preparation of difunctional compounds with high enantiomeric purity, of the type listed above and, in particular, but without any limitation being employed, of chiral 1,2-diols, from derivatives of the corresponding α-hydroxyacids, it being necessary for the said process to permit the mild reduction of the chiral substrate, so as to avoid racemization and having to offer the optimum conditions for rapid and easy extraction of the pure enantiomer sought after, especially while avoiding recourse to water, which unavoidably perturbs the extraction.

Accordingly, after lengthy and arduous investigations and experiments, the inventor has demonstrated, in a completely surprising and unexpected manner, that, in the synthesis of difunctional compounds of high enantiomeric purity by stoichiometric reduction with the aid of hydrides:

the reaction mixture is advantageously anhydrous (organic solvent), the stage of displacement of the difunctional compound sought after, from the complex which it forms with the conversion product of the hydride (borate) is advantageously performed with the aid of at least one coreactant:

substituted by at least one hydroxyl or thiol radical, preferably at least two, which also has a boiling point at normal atmospheric pressure ($P_{atm}$) higher than that of the difunctional compound sought after, and that it is also wholly judicious to perform a direct distillation making it possible to isolate the enantiomer sought after (di-OH, di-SH or mono-OH and mono-SH).

Thus, the present invention relates to a process for the preparation of difunctional compounds of high enantiomeric purity and of formula:

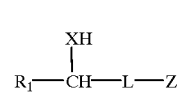

(If)

in which:

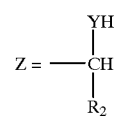

$R_1$ and $R_2$ are identical or different and denote hydrogen or an aliphatic and/or alicyclic and/or aromatic and/or heterocyclic and/or hydrocarbon radical, preferably a hydrogen or an alkyl, X and Y are identical or different and denote oxygen or sulphur, and L denotes a σ covalent single bond or a $C_1$ or $C_2$ alkyl group,
from pure chiral compounds corresponding to the formula (Id), which corresponds to the formula (If) in which:

with $R_2$ and Y as defined above, it being additionally possible for $R_2$ to denote an —$NH_2$, alkoxy, or alkylated S radical or:

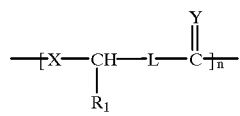

with n=1 to 1000, preferably 1 to 500 and, still more preferably, from 1 to 100, a process of the type of those involving a reduction of the compound (Id) with the aid of at least one reducing agent of the hydride type, characterized in that, in an anhydrous mixture:
 a) the reduction of the compound (Id) to a compound (If) is performed in an organic solvent medium,
 b) there is added to the reaction mixture at least one coreactant which is:
  substituted with at least one radical XH or YH, preferably at least two,
  capable of displacing the compound (If) in the intermediate originating from the preceding stage a), and
  possessing a boiling temperature at normal atmospheric pressure ($P_{atm}$) which is higher than that of the compound (If),
 c) the reaction mixture is distilled directly so as to recover the compound (If).

In accordance with the invention the starting materials of formula (Id) which are aimed at may be derivatives (esters, cyclic or other diners, oligo- or polycondensates, aldehydes, ketones) of α-, β- or γ-, preferably α-hydroxylated carboxylic acids and the sulphur homologues of these oxygen compounds.

When the starting substrate is a cyclic or other dimer or an oligo- or polycondensate, this corresponds to:

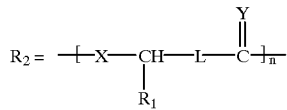

with n=1 to 1000. In the case of the cyclized dimers and oligo- and polycondensates, the group:

of the nth monomer is joined to the X of the first monomer.

The starting substrates of di-, oligo- and polymeric nature may, in fact, be considered to be precursors of the actual starting substrates of the reduction reaction (a), which are the monomers.

In particular, but without any limitation being implied, the present invention is aimed at the esters of α-hydroxycarboxylic acids, the D or L enantiomers of an ester of lactic acid being more particularly preferred.

The enantiomers of high optical purity aimed at by the invention are, of course, directly deducible from the above-mentioned compounds (Id). It will be sufficient merely to recall that the preferred chiral compounds (If) include 1,2-diols and, in particular, 1,2-propanediol and 1,2-butanediol.

It should be considered that the characteristic stages a), b) and c) of the process according to the invention are capable of accommodating some alternative forms relating to the chronology of their implementation. They are preferably successive.

The coreactant is one of the essential components of the process according to the invention. While meeting the specifications relating to the presence of at least one hydroxyl and/or one thiol among its substituents, and to its boiling temperature at $P_{atm}$, which is advantageously higher than that of the enantiomer (If), this coreactant is chosen from thiols such as thiosalicylic acid and/or 2- or 4-chlorobenzyl mercaptan and/or from alcohols such as aromatic alcohols and/or aliphatic alcohols and/or alicyclic alcohols and/or polyols, especially those of glucidic nature and/or carboxylic acids containing at least one hydroxyl group, preferably from aromatic alcohols and/or hydroxylated carboxylic acids containing from 4 to 10 carbons.

More precisely, the coreactant advantageously contains two radicals XH and/or YH, preferably from 2 to 4 atoms apart via the shortest route.

Substituted or unsubstituted diphenols, and in particular pyrocatechol, resorcinol and hydroquinone form a class of preferred coreactants.

This preference arises partly from the fact that such compounds are capable of forming a ring with the conversion product of the hydride, which blocks the formation of products If, by forming an intermediate at the outcome of the reduction (a). In fact, without wishing to be constricted by theory, it appears that the cyclization constitutes a mechanism which promotes the release of the products If.

Benzyl alcohol, 1-octanol, 1-dodecanol, glycerol, glycolic acid, tartaric acid and mandelic acid are to be found in another class of advantageous coreactants.

With regard to the anhydrous organic solvent medium, it is desirable that it should consist of polar solvents in accordance with a first alternative form of embodiment of the invention and, in particular, that the constituent(s) of the said medium should be chosen from glymes or their precursors, such as polyethylene glycols.

According to a second alternative form of embodiment, relating to the nature of the anhydrous organic solvent medium, the constituent(s) of the said medium is (are) selected from apolar solvents, preferably from optionally hydroxylated alkyls and/or aryls which are unsubstituted or substituted, especially with alkyls and/or halogens, benzene-related hydrocarbons such as xylene being particularly preferred.

In order to perfect the stage c of direct distillation of the reaction mixture, so as to isolate the enantiomer (If), an advantageous arrangement is provided according to which at least one of the constituents of the anhydrous organic solvent medium is such that it forms an azeotrope with the above-mentioned enantiomer (If). In fact, as soon as the latter is displaced from its bond with the conversion product of the hydride by virtue of the intervention of the coreactant, it can mix with the constituent of the solvent in question and thus be recoverable more easily and more rapidly, since the boiling temperature of the mixture at normal atmospheric pressure is lower than that of (If) and, as necessarily follows, than that of the coreactant and of the other residues of the reaction mixture.

Such an arrangement additionally provides the advantage of appreciably reducing the manufacturing cost of the process.

The hydride usable as reducing agent is chosen from metal hydrides, account being taken of technical and economic considerations. The above metals are preferably metals of column IIIA of the Periodic Classification, it being known that boron is particularly preferred and, still more preferably, the hydride selected is $NaBH_4$.

According to an advantageous characteristic the direct distillation stage c) is performed under vacuum, with concern for optimization.

Without any limitation being implied thereby, insofar as the substrates and the final products sought after are concerned, it may be indicated that in formulae (If) and (Id), advantageously, X and Y denote oxygen, L a σ single bond, $R_1$ is a $C_1-C_{10}$ alkyl, preferably methyl, ethyl or butyl, and $R_2$ is a $C_1-C_{10}$ alkoxy, preferably methoxy, ethoxy, butoxy or isobutoxy.

In fact (Id) is, for example, an alkyl, preferably methyl, lactate and (If) one of the enantiomers of 1,2-propanediol.

With regard to the methodology of the process according to the invention, the stoichiometry of the reactions is advantageously such that the hydride and the coreactant are in excess in relation to the substrate (If).

Thus, the (If):hydride normality ratio preferably varies from 1:1 to 1:2.

With regard to the coreactant, this normality ratio preferably varies from 1:2 to 1:3.

The process in accordance with the invention gives access to enantiomers of high optical purity (ee≧95%) and at low cost of manufacture when compared with those obtained previously. Hitherto limited for economic reasons, the outlets for, and the profitable uses of, such pure enantiomers ought to increase in number, in particular in the field of stereoselective synthesis, as synthesis intermediates or else in the pharmaceutical or agrochemical fields, as active ingredients and, finally, as a precursor in the preparation of special polymers of the liquid crystal type.

The alternative forms of the process according to the invention, including especially those relating to the operating method, and all the numerous advantages of the above-mentioned process, will clearly emerge from the examples of embodiment which follow, and from the results obtained, especially where the purities and the optical yields obtained are concerned.

EXAMPLES

Example 1

Synthesis of R(−)-1,2-Propanediol from R(+)D-Methyl Lactate 1.1 Reaction Scheme

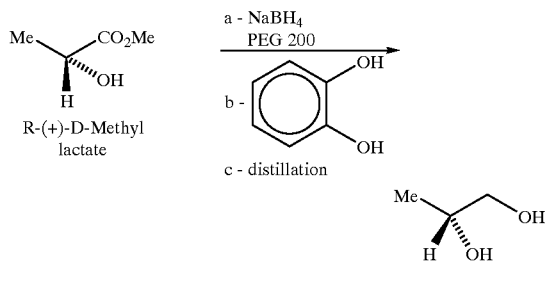

1.2 Raw Materials

| QUANTITIES | MOLES | NATURE - SOURCE - SPECIFICATIONS |
|---|---|---|
| 100 g | 0.96 (1 eq) | R(+)D-methyl lactate Rhone Poulenc – Melle factory – D = 97.48% |
| 47 g | 1.25 (1.3 eq) | $NaBH_4$ (Aldrich batch 56524-32) (98%) |
| 500 ml | | Polyethylene glycol 200 (Aldrich batch 56524-32) |
| 275 g | 2.50 (2.6 eq) | Pyrocatechol (Aldrich batch 24152) (98%) |

1.3 Equipment Employed 1.3.1 Reaction 2-1 round bottom flask fitted with a bulb for adding solid (endless screw), a condenser, a thermometer and a mechanical stirrer. An argon connection on the condenser.

1.3.2 Distillation

The condenser is replaced with a 20-cm Vigreux column+thermometer+condenser+collector+vacuum connection.

1.4 Operating Method 0 h

Methyl lactate is dissolved in polyethylene glycol 200 under argon. The borohydride is added slowly (over 8 hours) with stirring and under argon, so as to keep the temperature between 40 and 60° C. and to limit the foaming due to the release of hydrogen (after 2 h 25 min the addition is stopped for 1 h, during which the temperature spontaneously drops back to 28° C.).

After the end of the addition the reaction mixture is stirred overnight at ambient temperature (θ=28° C.).

24 h

The pyrocatechol is added in several portions (over 1 h) to the white and thick reaction mixture and then the whole is heated to 100° C. for 2 h. The mixture is cooled to 30° C., the condenser is replaced with a Vigreux column and a condenser and the whole is placed under vacuum and then heated. Six fractions were collected (methanol was not collected).

| 22 mbar | 85° C. | 1 = 2.54 g |
|---|---|---|
| | ↓ | 2 = 8.70 g |
| | 95° C. | 3 = 7.72 g |
| | | 4 = 11.06 g |
| 28 mbar | 104–95° C. | 5 = 15.97 g |
| 28 mbar | 90–97° C. | 6 = 19.27 g ($θ_{mass}$ = 160° C.) |
| | | Total of the fractions = 65.26 g. |
| | | Yield = 89.4%. |

1.5 Results

Quantitative and qualitative analyses of the fractions obtained by distillation are performed by gas phase chromatography on a chromatograph of Varian 6000 type. The derivative formation is of the O-TFA type.

The enantiomeric purity of the R(−)-1,2-propanediol is 97.16%, while that of the R(+)-methyl lactate employed was 97.48%. The optical yield is therefore 99.7%.

Example 2

Synthesis of S(+)-1,2-Propanediol from S(−)-Methyl Lactate

This Example 2 is similar to Example 1, the differences being that:

the starting material (Id) is S(−)-methyl lactate (Aldrich 98%, batch 82604-82), the solvent is polyethylene glycol 300 (Aldrich batch B 57339), the stoichiometric quantities have been divided by 10 when compared with Example 1.

After distillation, three fractions A, B and C are collected, consisting essentially of 1,2-propanediol, fraction C being, however, slightly richer in pyrocatechol than fractions A and B. Nuclear magnetic resonance analyses confirm the structure of the products obtained.

Gas phase chromatography makes it possible to establish that the chemical yield of propanediol is 99%, while the optical yield of S(+)-1,2-propanediol enantiomer is 100%.

Example 3

Synthesis of S(+)-Propanediol from S(−)-Methyl Lactate

Example 3 is identical with Example 2, the differences being that:

tartaric acid replaces pyrocatechol as coreactant, xylene is incorporated into the reaction mixture before the direct distillation stage c), a preliminary stage of evaporation before reduction (96° C., 16 millibars for 20 min) is applied so as to remove the undesirable by-products of low molecular weight which are present in the polyethylene glycol.

During the distillation a first methanol/p-xylene azeotrope is collected first of all, the methanol being a by-product of the reduction by the hydrides, and then, in a second step, a second propanediol/o-xylene azeotrope, at temperatures of 64 and 138° C. respectively.

Propanediol and xylene are not miscible with each other and are therefore separated very easily.

The chemical yield of propanediol is approximately 78%, while the optical yield attains a value of around 98%.

Example 4

Synthesis of S(+)-1,2-Propanediol from S(−)-Methyl Lactate

In this example the general methodology given in Examples 1 to 3 is repeated. This Example 4 corresponds substantially to Example 2 with a few modifications where the reactants and the operating method are concerned.

4.1 Reactants

Polyethylene glycol 300 is replaced with xylene, of the type marketed by Prolabo under the name "Normapur" (mixture of isomers).

4.2 Operating Method 0 h $\theta$=22° C. 500 ml of xylene are charged, and then the sodium borohydride as starting stock in order to form a heterogeneous mixture. Stirring at 197 rev/min.

10 min $\theta$=22° C. Cooling with a water bath is applied, methyl lactate is run in over 46 min.

55 min $\theta$=47° C. Exothermicity and considerable gas release.

$\theta$=55° C. Heating for 5 h 10 min.

6 h 05

$\theta$=58° C. Cooling.

6 h 35

$\theta$=38° C. The solution of P.C. (in methanol) is poured over 53 min into the reaction mixture (stirring at 437 rev/min). Increase in volume with much foam being formed.

7 h $\theta$=48° C. Appearance of a white precipitate.

The reaction mass thickens greatly.

100 ml of MeOH are added.

7 h 45

The pouring is finished. Heating and distillation of:

(i) methanol/p-xylene azeotrope ($\theta$=64° C.), (ii) propanediol/o-xylene azeotrope ($\theta$=134° C.).

Addition of 200 ml of xylene.

The crude propanediol is isolated by phase separation from the distillate=65.54 g.

This crude product is distilled:

o-xylene/propanediol azeotrope ($\theta$=134° C.), pure propanediol (at 25 mbar)=53.70 g ($\theta$=87° C.).

4.3 Results and Analyses

NMR confirms the structure of the products obtained and GC makes it possible to calculate, for the second fraction, a propanediol chemical yield of pure 100% and an optical yield of pure 100% of S(+)-propanediol.

This example with xylene is particularly advantageous, since it makes it possible to obtain enantiomers of high purity while using lower distillation temperatures than those employed in the other examples above.

I claim:

1. A process for the preparation of high enantiomeric purity compounds of formula:

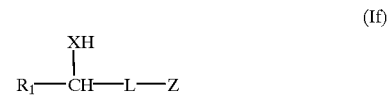

(If)

wherein:

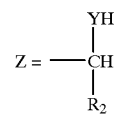

$R_1$ is an aliphatic, alicyclic, or aromatic hydrocarbon radical or a heterocyclic radical;

$R_2$ is hydrogen or an aliphatic, alicyclic, or aromatic hydrocarbon radical or a heterocyclic radical, $NH_2$, alkoxy, alkylated S radical, or

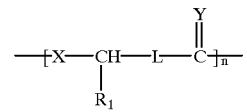

wherein n=1 to 1000;

X and Y are identical or different and are oxygen or sulfur; and

L is a o covalent single bond or a $C_1$ or $C_2$ group, from pure chiral compounds of formula (Id), which corresponds to the formula (If) in which:

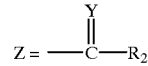

wherein $R_2$ and Y are as defined above, said process comprising sequentially carrying out the following steps in the order recited:

(a) contacting a compound of the formula (Id) with at least one hydride reducing agent in an anhydrous organic solvent medium at conditions effective to produce an intermediate comprising a compound of the formula (If);
(b) contacting the intermediate with at least one coreactant which is substituted with at least one XH or YH radical and which is capable of displacing the compound of the formula (If) from the intermediate; and
(c) directly distilling the organic solvent medium to recover the compound of the formula (If).

2. The process according to claim 1, wherein said coreactant has a higher boiling point at normal $P_{atm}$ than the compound of the formula (If).

3. The process according to claim 1, wherein $R_1$ is alkyl and $R_2$ is hydrogen or alkyl.

4. The process according to claim 1, wherein said coreactant comprises at least one of thiol, alcohol, and carboxylic acid containing at least one hydroxyl group.

5. The process according to claim 4, wherein said coreactant comprises at least one of thiosalicylic acid, 2- or 4-chlorobenzyl mercaptan, aromatic alcohol, aliphatic alcohol, alicyclic alcohol, polyol, and hydroxylated carboxylic acid containing 4 to 10 carbon atoms.

6. The process according to claim 5, wherein said coreactant is at least one of benzyl alcohol, 1-octanol, 1-dodecanol, glycerol, glycolic acid, tartaric acid, and mandelic acid.

7. The process according to claim 4, wherein said coreactant is a diol or a dithiol.

8. The process according to claim 7, wherein the hydroxyl or thiol groups in said diol or dithiol are 2 to 4 atoms apart from each other via the shortest route.

9. The process according to claim 8, wherein said coreactant is a substituted or unsubstituted diphenol.

10. The process according to claim 9, wherein said coreactant is pyrocatechol, resorcinol, or hydroquinone.

11. The process according to claim 1, wherein said anhydrous organic solvent medium comprises a polar solvent.

12. The process according to claim 11, wherein said polar solvent is a glyme or precursor thereof.

13. The process according to claim 12, wherein said polar solvent is a polyethylene glycol.

14. The process according to claim 1, wherein said anhydrous organic solvent medium comprises an apolar solvent.

15. The process according to claim 14, wherein said apolar solvent is an optionally hydroxylated and optionally substituted alkane or aromatic compound.

16. The process according to claim 15, wherein said apolar solvent is an aromatic compound substituted with at least one of alkyl and halogen.

17. The process according to claim 16, wherein said apolar solvent is xylene.

18. The process according to claim 1, wherein said anhydrous organic solvent medium comprises a solvent which forms an azeotrope with the compound (If).

19. The process according to claim 11, wherein said hydride reducing agent comprises a metal hydride.

20. The process according to claim 19, wherein the metal in said metal hydride is selected from Group IIIA of the Periodic Table of Elements.

21. The process according to claim 20, wherein said metal hydride is $NaBH_4$.

22. The process according to claim 11, wherein in formulae (If) and (Id):

X and Y are oxygen;
L is a σ single bond;
$R_1$ is a $C_1$–$C_{10}$ alkyl; and
$R_2$ is a $C_1$–$C_{10}$ alkoxy.

23. The process according to claim 22, wherein $R_1$ is methyl, ethyl, or butyl and $R_2$ is methoxy, ethoxy, butoxy, or isobutoxy.

24. The process according to claim 1, wherein the compound of the formula (Id) is methyl lactate and the compound of the formula (If) is 1,2-propanediol.

25. A process for the preparation of compounds of formula:

$$R_1-\underset{\underset{\displaystyle}{\overset{\displaystyle XH}{|}}}{CH}-L-Z \quad (If)$$

wherein:

$$Z = -\underset{\underset{\displaystyle R_2}{|}}{\overset{\overset{\displaystyle YH}{|}}{CH}}$$

$R_1$ is hydrogen or an aliphatic, alicyclic, or aromatic hydrocarbon radical or a heterocyclic radical;

$R_2$ is hydrogen or an aliphatic, alicyclic, or aromatic hydrocarbon radical or a heterocyclic radical, $NH_2$, alkoxy, alkylated S radical, or $$-\!\!\left[-X-\underset{\underset{\displaystyle R_1}{|}}{CH}-L-\overset{\overset{\displaystyle Y}{\|}}{C}-\right]_{\!n}$$

wherein n=1 to 1000;
X and Y are identical or different and are oxygen or sulfur; and
L is a σ covalent single bond or a $C_1$ or $C_2$ group, from compounds of formula (Id), which corresponds to the formula (If) in which:

$$Z = -\overset{\overset{\displaystyle Y}{\|}}{C}-R_2$$

wherein $R_2$ and Y are as defined above, said process comprising the steps of:
(a) reducing a compound of the formula (Id) in the presence of at least one hydride reducing agent in an anhydrous organic solvent medium to produce a compound of the formula (If);
(b) adding at least one coreactant selected from the group consisting of thiol, alcohol, and carboxylic acid containing at least one hydroxy group to the anhydrous organic solvent medium, wherein said coreactant has a higher boiling point at normal $P_{atm}$ than the compound of the formula (If); and
(c) directly distilling the organic solvent medium to recover the compound of the formula (If).

26. The process according to claim 25, wherein said steps (a) to (c) are carried out sequentially in the order recited.

27. A process for the preparation of compounds of formula:

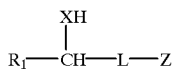 (If)

wherein:

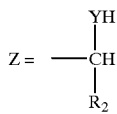

R$_1$ is an aliphatic, alicyclic, or aromatic hydrocarbon radical or a heterocyclic radical;

R$_2$ is hydrogen or an aliphatic, alicyclic, or aromatic hydrocarbon radical or a heterocyclic radical, NH$_2$, alkoxy, alkylated S radical, or

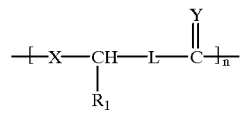

wherein n=1 to 1000;
X and Y are identical or different and are oxygen or sulfur;
at least one of X and Y is sulfur; and
L is a σ covalent single bond or a C$_1$ or C$_2$ group, from pure chiral compounds of formula (Id), which corresponds to the formula (If) in which:

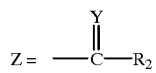

wherein R$_2$ and Y are as defined above, said process comprising the steps of:
(a) reducing a compound of the formula (Id) in the presence of at least one hydride reducing agent in an anhydrous organic solvent medium to produce a compound of the formula (If); and
(b) adding at least one coreactant selected from the group consisting of thiol, alcohol, and carboxylic acid containing at least one hydroxy group to the anhydrous organic solvent medium; and
(c) distilling the organic solvent medium to recover the compound of the formula (If).

28. The process according to claim 27, wherein said steps (a) to (c) are carried out sequentially in the order recited.

29. The process according to claim 27, wherein said coreactant has a higher boiling point at normal P$_{atm}$ than the compound of the formula (If).

30. A process for the preparation of high enantiomeric purity compounds of formula:

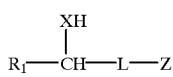 (If)

wherein:

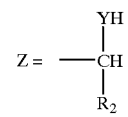

R$_1$ is an aliphatic, alicyclic, or aromatic hydrocarbon radical or a heterocyclic radical;

R$_2$ is hydrogen or an aliphatic, alicyclic, or aromatic hydrocarbon radical or a heterocyclic radical, NH$_2$, alkoxy, alkylated S radical, or

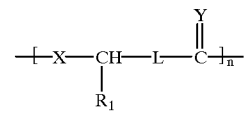

wherein n=1 to 1000;
X and Y are identical or different and are oxygen or sulfur; and
L is a σ covalent single bond or a C$_1$ or C$_2$ group, from pure chiral compounds of formula (Id), which corresponds to the formula (If) in which:

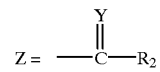

wherein R$_2$ and Y are as defined above, said process comprising the steps of:
(a) contacting a compound of the formula (Id) with at least one hydride reducing agent in an anhydrous organic solvent medium at conditions effective to produce an intermediate comprising a compound of the formula (If);
(b) contacting the intermediate with at least one coreactant selected from the group consisting of benzyl alcohol, 1-octanol, 1-dodecanol, glycerol, glycolic acid, tartaric acid, and mandelic acid; and
(c) distilling the organic solvent medium to recover the compound of the formula (If).

31. A process for the preparation of high enantiomeric purity compounds of formula:

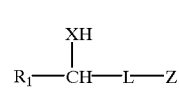 (If)

wherein:

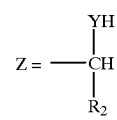

R$_1$ is an aliphatic, alicyclic, or aromatic hydrocarbon radical or a heterocyclic radical;

R$_2$ is hydrogen or an aliphatic, alicyclic, or aromatic hydrocarbon radical or a heterocyclic radical, NH$_2$, alkoxy, alkylated S radical, or

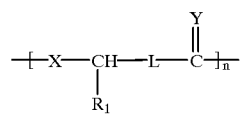

wherein n=1 to 1000;

X and Y are identical or different and are oxygen or sulfur; and

L is a σ covalent single bond or a $C_1$ or $C_2$ group, from pure chiral compounds of formula (Id), which corresponds to the formula (If) in which:

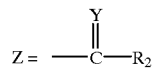

wherein $R_2$ and Y are as defined above, said process comprising the steps of:

(a) contacting a compound of the formula (Id) with at least one hydride reducing agent in an anhydrous organic solvent medium at conditions effective to produce an intermediate comprising a compound of the formula (If);

(b) contacting the intermediate with at least one diol or dithiol coreactant; and (c) distilling the organic solvent medium to recover the compound of the formula (If).

32. The process according to claim 31, wherein the hydroxyl or thiol groups in said diol or dithiol coreactant are 2 to 4 atoms apart from each other via the shortest route.

33. A process for the preparation of high enantiomeric purity compounds of formula:

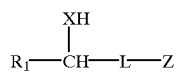

(If)

wherein:

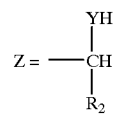

$R_1$ is an aliphatic, alicyclic, or aromatic hydrocarbon radical or a heterocyclic radical;

$R_2$ is hydrogen or an aliphatic, alicyclic, or aromatic hydrocarbon radical or a heterocyclic radical, $NH_2$, alkoxy, alkylated S radical, or

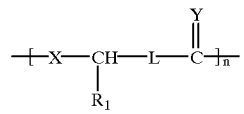

wherein n=1 to 1000;

X and Y are identical or different and are oxygen or sulfur; and

L is a σ covalent single bond or a $C_1$ or $C_2$ group, from pure chiral compounds of formula (Id), which corresponds to the formula (If) in which:

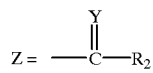

wherein $R_2$ and Y are as defined above, said process comprising the steps of:

(a) contacting a compound of the formula (Id) with at least one hydride reducing agent in an anhydrous organic solvent medium at conditions effective to produce an intermediate comprising a compound of the formula (If);

(b) contacting the intermediate with at least one substituted or unsubstituted diphenol coreactant; and (c) distilling the organic solvent medium to recover the compound of the formula (If).

34. The process according to claim 33, wherein said coreactant is pyrocatechol, resorcinol, or hydroquinone.

* * * * *